(12) United States Patent
Shane et al.

(10) Patent No.: US 8,802,143 B2
(45) Date of Patent: *Aug. 12, 2014

(54) METHOD FOR TREATING NEURODEGENERATIVE DISORDERS WITH ORAL DOSAGE FORMULATION CONTAINING BOTH IMMEDIATE-RELEASE AND SUSTAINED-RELEASE DRUGS

(75) Inventors: Guang-Tzuu Shane, Taipei (TW); Chien-Fen Chen, Taipei (TW); Chuen-Lin Din, Taipei (TW); Hui-Ling Tsai, Hukou Township (TW); Pei-Chen Tsai, Taipei (TW)

(73) Assignee: Center Laboratories, Inc., Taipei (TW)

( * ) Notice: Subject to any disclaimer, the term of this patent is extended or adjusted under 35 U.S.C. 154(b) by 503 days.

This patent is subject to a terminal disclaimer.

(21) Appl. No.: 13/071,520

(22) Filed: Mar. 25, 2011

(65) Prior Publication Data

US 2011/0171302 A1    Jul. 14, 2011

Related U.S. Application Data

(63) Continuation-in-part of application No. 13/063,462, filed as application No. PCT/CN2010/001519 on Sep. 29, 2010.

(60) Provisional application No. 61/247,057, filed on Sep. 30, 2009.

(51) Int. Cl.
*A61K 9/44* (2006.01)

(52) U.S. Cl.
USPC .......................................................... 424/467

(58) Field of Classification Search
None
See application file for complete search history.

(56) References Cited

U.S. PATENT DOCUMENTS

| 6,682,759 B2 | 1/2004 | Lim et al. |
| 7,255,876 B2 | 8/2007 | Shinoda et al. |
| 7,619,007 B2 * | 11/2009 | Went et al. ................. 514/662 |
| 2003/0144271 A1 * | 7/2003 | Shulman ................. 514/214.03 |
| 2005/0232990 A1 | 10/2005 | Boehm et al. |
| 2009/0023778 A1 * | 1/2009 | Kimura et al. .............. 514/319 |
| 2009/0124659 A1 | 5/2009 | Moebius |

FOREIGN PATENT DOCUMENTS

| CN | 101166543 A | 4/2008 |
| CN | 101247795 A | 8/2008 |

OTHER PUBLICATIONS

Patnaik et al. (The role of pharmacogenetics in treating central nervous system disorders, Experimental Biology and Medicine 2008, 233:1504-1509).*
Dimitri et al. Neuropathology, http://neuropathology-web.org/chapter6/chapter6aMs.html, see attached).*

* cited by examiner

*Primary Examiner* — Snigdha Maewall
(74) *Attorney, Agent, or Firm* — Chih Feng Yeh; Huntington IP Consulting Co., Ltd.

(57) ABSTRACT

Disclosed herein is a method for treating patient suffering from a disorder related to central nervous system with an oral dosage formulation that contains both sustained-release and immediate-release drugs. The sustained-release drug in the oral dosage formulation is memantine, and the formulation provides an average blood level $C_{max}$ of the memantine in a range of about 10-24 ng/mL during an average $T_{max}$ of about 10-45 hours. The immediate-release drug in the oral dosage formulation is an acetylcholinesterase inhibitor (AChEI), and the formulation provides an average blood level $C_{max}$ of the AChEI in a range of about 12-38 ng/mL during an average $T_{max}$ of less than about 4 hours.

8 Claims, No Drawings

METHOD FOR TREATING NEURODEGENERATIVE DISORDERS WITH ORAL DOSAGE FORMULATION CONTAINING BOTH IMMEDIATE-RELEASE AND SUSTAINED-RELEASE DRUGS

CROSS REFERENCES

This application is a continuation-in-part of application Ser. No. 13/063,462, filed on Mar. 10, 2011, which is the national stage of international Application No: PCT/CN2010/001519, filed on Sep. 29, 2010; which claims the benefit of Provisional Application No. 61/247,057, filed on Sep. 30, 2009.

BACKGROUND OF THE INVENTION

1. Field of the Invention

The present disclosure in general relates to methods for treating neurodegenerative disorders. More particularly, the disclosure invention relates to methods for treating neurodegenerative disorders with an oral dosage formulation that contains both immediate-release and sustained-release drugs.

2. Description of Related Art

Neurodegenerative disorders are conditions in which cells of the brain and spinal cord are lost, which may eventually lead to central nervous system (CNS)-related dysfunction, which includes, for example, Alzheimer's disease, Parkinson's disease, Huntington's disease, etc.

Initial treatment for neurodegenerative disorders is dependent on diagnosis of the underlying condition. Currently, few therapies are available for the treatment of most neurodegenerative diseases. Therapy designed to enhance cholinergic function by inhibiting acetylcholinesterase (AChE) or by attenuating N-methyl-D-aspartate (NMDA) receptor function using 1-aminocyclohexane derivatives (e.g., memantine) has been adopted to stabilize cognitive function of the dementia patient. Recently, treatment with both 1-aminocyclohexane derivatives and acetylcholinesterase inhibitors (AChEI) have been hypothesized and demonstrated in U.S. Patent application No. 2009/0124659, which was filed by Moebius on Feb. 27, 2008. Moebius suggested that the novel combination of 1-aminocyclohexane derivatives and AChEI provides super additive effect to relieve the symptoms of dementia. The combination of drugs, are provided in one composition or in two different compositions for simultaneously or sequentially ingestion.

Current dose regimens for 1-aminocyclohexane derivatives and AChEI require patients to take more than one dose a day. This is undesirable for compliance decreases as the frequency of taking a drug increases. It also poses a difficulty for patients who start to lose cognitive function including memory to follow the dose regimens of drugs and thereby would further diminish the effects of treatment. Moreover, it is well known that certain medical conditions are most desirably treated with a dosage form that provides both immediate and extended therapeutic effects while reducing the number of doses necessary, thereby making therapy more convenient. Known examples of pharmaceutical formulations which provide both immediate and sustained-release of an active pharmaceutical ingredient may refer to U.S. Pat. No. 7,255,876 B2 to Shinoda et al. and U.S. Pat. No. 6,682,759 B2 to Lim et al. Therefore, there exists a need in this field a simple and convenient course of treatment for CNS-related dysfunction, such as dementia.

Our previous invention addressed such need by providing an improved oral formulation of the two drugs proposed by Moebius (Supra), i.e., 1-aminocyclohexane derivatives and AChEI. In the improved formulation, one drug is designed to be released immediately upon ingestion whereas the other is designed to be released over an extended period of time. With this proposed formulation, the course of treatment for CNS-related dysfunction such as dementia is greatly simplified by eliminating the need for a patient to take several pills either simultaneously or sequentially during the course of treatment, hence would greatly improve the effects of drugs in delaying and/or preventing the onset or progression of the disease.

However, 1-aminocyclohexane derivatives and AChEI are known to cause side effects such as dizziness, headache, fatigue, asthenia, somnolence, chills, insensible sweats, anorexia, gastrointestinal discomfort, nausea, and/or vomiting. As such, there is a need for unique formulation approaches that provide the desired therapeutic effects while minimizing the occurrence and/or severity of these and other undesired side effects.

SUMMARY

As embodied and broadly described herein, disclosure herein features a novel method useful for treating disorders related to central nervous system (CNS) in a subject, particularly, the human with a CNS disorder such as dementia, Alzheimer's disease, Parkinson's disease, Huntington's disease and the like.

In one aspect, the present disclosure is directed to methods for treating a patient suffering from a CNS disorder with an oral dosage formulation comprising a sustained-release portion of a first compound and an immediate-release portion of a second compound. According to the principles and spirits of the present disclosure, the oral dosage formulation may be formulated to meet the steady state blood levels required for the treatment of the CNS disorder while ameliorating the side effects experienced by the patient.

According to embodiments of the present disclosure, the formulation provides an average blood level $C_{max}$ of the first compound in a range of about 10-24 ng/mL during an average $T_{max}$ of about 10-45 hours, and an average blood level $C_{max}$ of the second compound in a range of about 12-38 ng/mL during an average $T_{max}$ of less than about 4 hours. The first compound is memantine, a salt, a solvate, or a mixture thereof and is present in an amount of about 1-80 mg in the formulation, whereas the second compound is an acetylcholinesterase inhibitor (AChEI) and is present in an amount of about 1-160 mg in the formulation.

The formulation may exhibit an $AUC_{0-t}$ of the first compound in a range of about 1300-1800 ng·h/mL and an $AUC_{0-t}$ of the second compound in a range of about 700-1000 ng·h/mL, respectively measured after 156 hours.

Moreover, according to embodiments of the present disclosure, the oral dosage formulation may be administered once a day or once every two days, which is advantageous at least in terms of patient compliance.

According to specific embodiments of this disclosure, the sustained-release portion is in the form of pellets having sustained-release films coated thereon, and the immediate-release portion is in the form of granules. To produce the oral formulation of this invention, the sustained-release portion and the immediate-release portion are mixed with at least one binder and then compressed to form tablets or caplets.

According to certain examples, the first compound is present in an amount of about 5-60 mg, and the second compound is present in an amount of about 5-30 mg. In some example, the first compound is present in an amount of about 16-24 mg and the second compound is present in an amount of about 8-12 mg. In one specific example, the first compound is present in an amount of about 20 mg and the second compound is present in an amount of about 10 mg.

In one specific example, the first compound is memantine. In another specific example, the first compound is memantine hydrochloride.

According to specific embodiments of this disclosure, the second compound or AChEI useful for the described purpose is any of galantamine, tacrine, donepezil, rivastigmine, huperzine A, zanapezil, ganstigmine, phenserine, phenethylnorcymserine, cymserine, thiacymserine, SPH 1371, ER 127528, RS 1259, a salt or a solvate thereof, an enantiomer thereof, a salt or a solvate of the enantiomer or a mixture thereof. In one specific example, AChEI is donepezil. In another example, AChEI is donepezil hydrochloride.

By administering a patient the present oral dosage formulation on a daily (once per day) or bi-daily (once every two days) basis, the course of a treatment for a subject with a CNS disorder such as dementia or Alzheimer's disease is greatly simplified thereby enhancing the patient compliance. For example, the number of tablets the subject required to take daily may be substantially reduce to a significantly low number of one or even less than one, such as half a tablet per day or one tablet for every two days, in accordance with some examples of this disclosure. Also, by respectively providing adequate amounts of the first and second compounds in the sustained-release and the immediate-released portions, it is possible to achieve the desired therapeutic effect as well as ameliorate the side effects experienced by the patient.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

DETAILED DESCRIPTION

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The practices of this invention are hereinafter described in detail with respect to a method for treating a patient suffering from a CNS disorder with an oral dosage formulation. Results of pilot pharmacokinetic study, as described hereinbelow, show that the oral dosage formulation, particularly, an oral dosage formulation that contains both immediate-release and sustained-release drugs, may provide the desired therapeutic effects while ameliorating the undesired side effects.

As used in the present disclosure, the term "$C_{max}$" refers to the maximum concentration of an active compound or drug (e.g., memantine or AchEI) in the blood plasma, whereas the term "$T_{max}$" means the time to achieve the maximum plasma concentration of said active compound or drug. The term "$AUC_{0-t}$" refers to an area under the curve from zero to the last measured time point of a measurable drug concentration.

In accordance with embodiments of the present disclosure, the oral dosage formulation provides an average blood level $C_{max}$ of the first compound in a range of about 10-24 ng/mL during an average $T_{max}$ of about 10-45 hours, and an average blood level $C_{max}$ of the second compound in a range of about 12-38 ng/mL during an average $T_{max}$ of less than about 4 hours. The first compound is memantine, a salt, a solvate, or a mixture thereof and is present in an amount of about 1-80 mg in the formulation, whereas the second compound is an acetylcholinesterase inhibitor (AChEI) and is present in an amount of about 1-160 mg in the formulation.

In accordance with other embodiments of the present disclosure, the average blood level $C_{max}$ of the first compound is in a range of about 11-22 ng/mL during the average $T_{max}$ of about 12-42 hours, and the average blood level $C_{max}$ of the second compound is in a range of about 14-35 ng/mL during the average $T_{max}$ of less than about 3 hours. In accordance with still yet other embodiments of the present disclosure, the average blood level $C_{max}$ of the first compound is in a range of about 15-20 ng/mL during the average $T_{max}$ of about 20-24 hours, and the average blood level $C_{max}$ of the second compound is in a range of about 18-31 ng/mL during the average $T_{max}$ of less than about 2 hours.

In pharmacokinetic (PK) studies, $AUC_{0-t}$ of the active compound or drug is often used for assessing the efficacy or the bioequivalence of the active compound/drug. In accordance with the present disclosure, the blood level of the active compound is last measured at 156 hours after the ingestion of the oral dosage formulation. In accordance with embodiments of the present disclosure, the formulation may provide an $AUC_{0-t}$ of the first compound in a range of about 1300-1800 ng·h/mL and an $AUC_{0-t}$ of the second compound in a range of about 700-1000 ng·h/mL, respectively measured for a period of 156 hrs.

Memantine hydrochloride is currently sold under various brand names including EBIXA® and NAMENDA®. For daily dosage containing more than 5 mg of memantine hydrochloride, it is generally advised that the formulation shall be administered twice daily. For example, if the patient is prescribed to take 15 mg of memantine hydrochloride daily, he/she is advised to take a dose of 10 mg in the morning and a dose of 5 mg in the afternoon. According to embodiments of this disclosure, total daily dosage of memantine hydrochloride may be 5, 10, 15 or 20 mg/day.

In contrast, the oral dosage formulation is administered once a day or once every two days according to the present methods. In this regard, the method according to embodiments of the present disclosure may advantageously simplify the course of the treatment while reduce the occurrence and/or severity of at least one of the side effects.

The term "salt" refers herein as a salt which is formed by the interaction of a base (such as memantine or donepezil in this disclosure) with an acid, including organic or inorganic types of acids such as hydrochloric acid, hydrobromic acid, hydroiodic acid, perchloric acid, methylsulfonic acid, sulfuric acid, nitric acid, phosphoric acid, acetic acid, propionic acid, glycolic acid, pyruvic acid, malonic acid, succinic acid, maleic acid, fumaric acid, tartaric acid, citric acid, benzoic acid, carbonic acid, cinnamic acid, methanesulfonic acid, ethanesulfonic acid, hydroxyethanesulfonic acid, benzenesulfonic acid, p-toluene sulfonic acid, cyclohexanesulfamic acid, salicyclic acid, p-aminosalicyclic acid, 2-phenoxybenzoic acid and 2-acetoxybenzoic acid. In one preferred example, the salt is memantine hydrochloride. In another example, the salt is donepezil hydrochloride. The term "solvate" herein refers to a complex formed by the interaction of a compound (such as memantine or donepezil in this disclosure) with surrounding solvent molecules, such as water, ethanol, and etc. In one example, the solvate of a first compound is a memantine hydrate.

The term "acetylcholinesterase inhibitor" or "AChEI" refers herein to a drug that enhances the functions of cholinergic neurons by inhibiting the activity of acetylcholinesterase (AChE). AChEI useful for the described purpose is any of galantamine, tacrine, donepezil, rivastigmine, huperzine A, zanapezil, ganstigmine, phenserine, phenethylnorcymserine, cymserine, thiacymserine, SPH 1371, ER 127528, RS 1259, a salt or a solvate thereof, an enantiomer thereof, a salt or a solvate of the enantiomer or a mixture thereof. Suitable salts of AChEI may be formed by the interaction of any AChEI compound with an acid, such as the acids described above. In one specific example, AChEI is donepezil hydrochloride ((R,S)-1-benzyl-4-[(5,6-dimethoxy-1-indanone)-2-yl]-methyl-piperidine hydrochloride).

The term "sustained-release" herein refers to the release of the therapeutic compound occurs over an extended period of time leading to lower peak plasma concentrations and/or is directed to a prolonged $T_{max}$ as compared with "immediate-release" portion containing the same compound. The sustained-release portion of the dosage formulation is designed to deliver memantine, a salt, or a solvate thereof to the digestive system of a subject continuously over a period of time for at least an hour and preferably more than several hours. In one example, the dissolution rate is slow enough that at least about 60% of memantine, a salt or a solvate thereof remains unreleased after two hours and more preferably at least about 70% of memantine, a salt or a solvate thereof remains unreleased after two hours. In general, the memantine, a salt, or a solvate thereof will be at least 80% released within 12 hours, and will be at least 90% released within 24 hours.

The memantine, a salt or a solvate thereof in the sustained-release portion of the formulation is retained in a matrix that is composed by at least one polymer that includes, but is not limited to, methylcellulose (MC), ethyl cellulose (EC), hydroxypropyl cellulose (HPC), hydroxypropyl methylcellulose (HPMC), carboxyl methylcellulose (CMC), microcrystalline cellulose, cellulose acetate, cellulose propionate, cellulose acetate propionate, cellulose acetate butyrate, cellulose acetate phthalate, cellulose triacetate, polymethyl methacrylate, polyethyl methacrylate, polyvinyl alcohol, polyvinyl acetate, polyvinyl alcohol-ethylene glycol, carbomer, polyethylene glycol (PEG) and a combination thereof. Suitable polymer(s) for producing the matrix are those sold under the trademark that includes, but is not limited to, CELPHERE® CP708, EUDRAGIT®, OPADRY®, ACRYL-EZE®, SURELEASE®, METHOCEL®, ETHOCEL®, or SURETERIC®.

The sustained-release (SR) portion may be prepared by mixing memantine, a salt, a solvate, or a mixture thereof with the matrix polymer described above and suitable binders, then directly compressing the mixture into SR tablets.

Alternatively, the sustained-release portion may contain sustained-release fine particles or pellets that are produced by any known method such as wet granulation or dry granulation method. In one example, the sustained-release fine particles or pellets are produced by wet granulation, particularly, fluid bed granulation. Wet granulation generally involves the steps of mixing the drug, at least one of the matrix polymer as described above and a binder solution; drying the moist granules; and screening through a suitable sieve to produce particles with desired sizes. Useful binders include, but are not limited to, acacia, tragacanth, alginic acid, sodium alginate, carbomer, carboxymethylcellulose sodium, carrageenan, cellulose acetate phthalate, ceratonia, copovidone, dextrates, dextrin, dextrose, methylcellulose, ethylcellulose, carboxymethyl cellulose, hydroxypropyl methyl cellulose, hydroxyethyl cellulose; hydroxyethylmethyl cellulose; hydroxypropyl cellulose; hydroxypropyl starch; hypromellose, gelatin, starch, sucrose, lactose, magnesium aluminum silicate, maltodextrin, maltose, microcrystalline cellulose, polyvinyl pyrrolidone, polyacrylamide, povidone and pregelatinized starch. In certain examples, the sustained-release portion is prepared by mixing memantine, a salt, a solvate or a mixture thereof with a sugar sphere made of microcrystalline cellulose (e.g., CELPHERE® CP708), and at least one other matrix polymer as described above, to form granules or pellets that contain memantine. Then, each of the memantine containing granules or pellets is coated with a sustained-release film to produce the sustained-release portion or the SR portion. In some examples, the sustained-release film contains at least a matrix polymer described above (e.g., EUDRAGIT® NE30D and HPMC), and a diluent (e.g., talc). In other examples, the sustained-release film contains at least EUDRAGIT® NE30D, SURELEASE®, HPMC, and titanium dioxides.

Other useful diluents include, but are not limited to, ammonium alginate, calcium carbonate, calcium phosphate dibasic, calcium phosphate tribasic, calcium sulfate, cellulose, cellulose acetate, compressible sugar, dextrates, dextrin, dextrose, erythritol; ethylcellulose, fructose, fumaric acid, glyceryl palmitostearate, lactitol, lactose, mannitol, magnesium carbonate, magnesium oxide, maltodextrin, maltose, microcrystalline cellulose, polydextrose, polymethacrylates, sodium chloride, sorbitol, starch, sucrose, sugar spheres, ARBOCEL A300®; LUDIPRESS®; and SUPER TAB®.

Optionally, the SR portion (such as the SR tablets, SR pellets and the SR granules) may be further coated with a protective coating to delay the release of the active ingredient therein. The protective coating may comprise at least one of the matrix polymers as described above. In one example, the protective coating comprises hydroxymethyl cellulose and polyethylene glycol (PEG). In another example, the protective coating comprises triethyl citrate (TEC) and talc. The SR coating and the protective coating may be applied as a film respectively deposited over the sustained-release pellets and the sustained-release portion, by any known techniques such as spraying, dipping, or pan-coating.

The immediate-release portion of the dosage formulation is designed to rapidly disintegrate upon contacting a fluid such as water and allow fast leaching out of AChEI to the environment continuously over a short period of time, such as several minutes or in an hour. The dissolution rate is fast enough that at least 80% of AChEI is released within the first 60 minutes. In general, at least 90% of AChEI will be released within 2 hours.

In one example, the AChEI in the immediate-release portion is in a form of an immediate-release particle or granule which could be mixed with the SR portion (such as the SR pellets and SR granules) and at least one binder, and then compressed into tablets or caplets.

Alternatively, the AChEI may be applied as a thin film deposited over the outer surface of the sustained release portion (such as the SR tablets). Still alternatively, the oral dosage formulation could be a tablet constructed in two or more layers with at least one layer being the IR portion while one of the other layers thereof being the SR portion.

The immediate-release particles may be produced by any known method, such as dry or wet granulation method as described above. In one example, AChEI is mixed with disintegrants and/or binders, and adsorbents and then the mixture is subjected to either fluid bed granulation or spray drying to produce particles with desired immediate-release property. Examples of disintegrants include, but are not limited to, cross-linked polyvinyl pyrrolidone or crospovidone, starch derivatives such as carboxymethyl cellulose and cellulose derivatives; calcium alginate; carboxymethylcellulose calcium; carboxymethylcellulose sodium; croscarmellose sodium; docusate sodium; hydroxypropyl cellulose; magnesium aluminum silicate; methylcellulose; polacrilin potassium; sodium alginate; sodium starch glycolate and pregelatinized starch. Examples of adsorbents include, but are not limited to, aluminum hydroxide adjuvant; aluminum oxide; aluminum phosphate adjuvant; attapulgite; bentonite; powdered cellulose; colloidal silicon dioxide; hectorite; kaolin; magnesium aluminum silicate; magnesium carbonate; microcrystalline cellulose; pectin; polycarbophil; and saponite. At least 50% of the immediate-release particles thus prepared have a size that may pass an 80-mesh sieve; preferably, a 60-mesh sieve; more preferably, a 40-mesh sieve; and most preferably, a 20-mesh sieve.

According to specific embodiments, the sustained-release portion and the immediate-release portion respectively prepared by steps as described above are combined with binders (such as those described above) and lubricants to form the oral dosage formulation of this disclosure. Suitable lubricants include, but are not limited to, calcium stearate; glyceryl behenate; glyceryl palmitostearate; magnesium lauryl sulfate; magnesium stearate; polyethylene glycol; potassium benzoate; sodium lauryl sulfate; sodium stearyl fumarate; stearic acid; talc and zinc stearate.

Optionally, the dosage formulation may also contain at least one suitable glidant; examples of which include, but are not limited to, calcium phosphate, tribasic; calcium silicate; cellulose, powdered; colloidal silicon dioxide; magnesium silicate; magnesium trisilicate; silicon dioxide; starch and talc. Still optionally, the dosage formulation may additionally contain suitable pigments such as titanium dioxide.

The oral dosage formulation of this disclosure may be in a form of tablets, caplets, bi-layer tablets, film-coated tablets, pills, capsules, or the like. Tablets in accordance with this disclosure can be prepared by any mixing and tabletting techniques that are well known in the pharmaceutical formulation industry. In some examples, the dosage formulation is fabricated by direct compressing the respectively prepared sustained-release portion and the immediate-release portion by punches and dies fitted to a rotary tabletting press, ejection or compression molding or granulation followed by compression. In one example, the dosage form is a single layer tablet containing therein both the sustained-release and the immediate-release portions. In another example, the dosage form is a tablet containing two layers, with one layer being the immediate-release portion and the other layer being the sustained-release portion. In still another example, the dosage form is a film-coated tablet having a sustained-release portion and a thin film of the immediate-release portion deposited over the outer surface of the sustained-release portion. The immediate-release portion may be applied as a coating over the sustained-release portion by any known techniques such as spraying, dipping, or pan-coating, or as an additional layer by tabletting or compressing in the same manner as the sustained-release portion. In some examples, the tablet is a scoring tablet having a score line at the center of the tablet for breaking the tablet into two equal halves when necessary. In other examples, the oral dosage formulation is in a form of capsule containing therein both the sustained-release particles or pellets of the first compound (i.e., memantine, a salt, a solvate, or a mixture thereof) and the immediate-release particles or pellets of the second compound (i.e., AChEI, a salt or a solvate thereof, an enantiomer thereof, a salt or a solvate of the enantiomer or a mixture thereof). According to some embodiments of the present disclosure, SR portions (e.g., SR pellets, in which each pellet contains a SR film coated thereon) and IR granules are mixed with polyvinyl pyrrolidone (PVPPXL-10®) and magnesium stearate, and then the mixture is compressed to obtain a single layer tablet containing therein both the sustained-release and the immediate-release portions.

According to the methods of the present disclosure, the oral dosage formulations described herein are administered to a patient at therapeutically effective doses, preferably, with minimal toxicity. Specific examples of the oral dosage formulation of this disclosure include about 1-80 mg of memantine, a salt, a solvate or a mixture thereof, such as 5-60 mg, or 16-24 mg of memantine, a solvate or a mixture thereof; and about 1-160 mg of AChEI, a salt or a solvate thereof, an enantiomer thereof, a salt or a solvate of the enantiomer or a mixture thereof, such as 5-30 mg, or 8-12 mg of AChEI, a salt or a solvate thereof, an enantiomer thereof, a salt or a solvate of the enantiomer or a mixture thereof. In one example, memantine, a solvate or a mixture thereof is present in an amount of about 20 mg/dosage formulation, and AChEI, a salt or a solvate thereof, an enantiomer thereof, a salt or a solvate of the enantiomer or a mixture thereof is present in an amount of about 10 mg/dosage formulation.

It must be noted that as used herein and in the appended claims, the singular forms "a", "an", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

The following Examples are provided to illustrate certain aspects of the present invention and to aid those of skilled in the art in practicing this invention. These Examples are in no way to be considered to limit the scope of the invention in any manner.

EXAMPLES

Example 1

Production of IR/SR Tablets and In Vitro Dissolution Performance of the Produced Tablets In this example, the sustained-release (SR) portion and the immediate-release (IR) portion were separately produced in accordance with steps and conditions described in examples 1.1 and 1.2. The tablet containing both the IR and SR portions (or the IR/SR Tablet), was subsequently made by compressing the IR and SR portions together in accordance with the conditions set forth in Examples 1.3 and 1.4.

1.1 Production of SR Portion

In operation, the SR portion was produced by forming a memantine pellet first; then followed by coating the thus made memantine pellet with a sustained release film (i.e., SR film) outside each pellet. The memantine pellets were produced by mixing the ingredients listed in the SR pellet formulation in Table 1 in a fluid bed machine under processing parameters set as follows:

| Processing Parameters for Forming Memantine Pellet | |
|---|---|
| Temperature | 45° C. |
| Air Pressure | 0.45 bar |

-continued

| Processing Parameters for Forming Memantine Pellet | |
|---|---|
| Atomizing air | 1.00 bar |
| Flow speed | 26 rpm (6 g/min) |
| Pellet temperature | 28.5° C. |

Each of the thus prepared memantine pellets was then coated with a sustained-release film in accordance with the SR-coating formulation-1 and SR-coating formulation-2 respectively listed in Table 1 and Table 2, and thereby producing SR portions 1 and 2. The processing parameters for coating SR-coating formulation-1 and SR-coating formulation-2 respectively onto the memantine pellets to form the respective SR portions (i.e., SR portion 1 or 2) are respectively set as follows:

| Processing Parameters for Forming SR-Film Coated Memantine Pellet-1 | |
|---|---|
| temperature | 30° C. |
| Air Pressure | 0.48 bar |
| Atomizing air | 1.20 bar |
| Flow speed | 14 rpm (4 g/min) |
| Pellet temperature | 22° C. |

| Processing Parameters for Forming SR-Film Coated Memantine Pellet-2 | |
|---|---|
| temperature | 36° C. |
| Air Pressure | 0.5 bar |
| Atomizing air | 1.20 bar |
| Flow speed | 14 rpm (4 g/min) |
| Pellet temperature | 26° C. |

1.2 Production of IR Portion

The IR portions were prepared by mixing the ingredients listed in the IR granule formulation in Table 1 or 2 in accordance with steps as described below. Briefly, donepezil and microcrystalline cellulose (i.e., MCC KG802) were mixed in equal amount to form a mixture that passed an 80-mesh sieve. Then, the remaining microcrystalline cellulose, other excipient(s) including non-soluble pregelatinized starch (i.e., PC-10) were added thereto, followed by the addition of water to form wet granule that passed a 20-mesh sieve. The granules were subsequently dried at 50° C. for 3 hours.

1.3 Production of IR/SR Tablet-1 Formulation

PVPPXL-10 and the SR portion 1 of example 1.1 were added to the dry granules of example 1.2 and mixed at a speed at 22 rpm for 10 minutes. Then, magnesium stearate (i.e., a lubricant) was added, and the resulted mixture was subsequently compressed into tablets with scoring and thereby produced IR/SR tablet-1, and tablets having a hardness of 5 Kg, 6 Kg and 8 kg were produced.

TABLE 1

| Unit dose composition of IR/SR Tablet-1 (342 mg Tablet) | |
|---|---|
| Ingredients | Weight, mg |
| SR Pellet Formulation | |
| CELPHERE ® CP305[a] | 100 |
| Memantine HCl | 20 |
| HPMC E6 | 6.0 |
| PEG 400 | 0.6 |
| Subtotal | 126.6 |
| SR-Coating-1 Formulation | |
| Eudragit NE30D[b] | 31.7 |
| Talc | 31.7 |
| HPMC | 0.8 |
| Total | 190.7 |
| IR Granule Formulation | |
| Donepezil HCl | 10 |
| MCC CEOLUS ® KG802[a] | 115 |
| PC-10 | 15 |
| Total | 140 |
| IR/SR Tablet-1 Formulation | |
| SR Portion | 190 |
| IR Portion | 140 |
| PVPP XL-10 | 10 |
| Magnesium Stearate | 2 |
| Total | 342 |

[a]CELPHERE ® CP305 (300-500 μm) and MCC CEOLUS ® KG802 were purchased from Asahi Kasei Chemicals Corporation, (Tokyo, Japan)
[b]EUDRAIGIT ® NE30D was purchased from Evonik Röhm GmbH (Darmstadt, Germany).
HPMC = hydroxypropyl methyl cellulose
PEG 400 = polyethylene glycol 400
MCC = microcrystalline cellulose
PVPP XL-10 = polyvinyl polypyrrolidone, Copovidone 1.4 Production of IR/SR Tablet-2 Formulation IR/SR tablet-2 were produced in accordance with similar steps described in Example 1.3, except SR portion 2 of example 1.1 was used in this example; and tablets (about 310 mg) having a hardness of 5-6 Kg were produced. The unit dose formulation of IR/SR tablet-2 is given in Table 2.

TABLE 2

| Unit dose composition of IR/SR Tablet-2 (310 mg Tablet) | |
|---|---|
| Ingredients | Weight, mg |
| SR Pellet Formulation | |
| CELPHERE ® CP305[a] | 100 |
| Memantine HCl | 20 |
| HPMC E6 | 6.0 |
| PEG 400 | 0.6 |
| Subtotal | 126.6 |
| SR-Coating-2 Formulation | |
| Eudragit NE30D[b] | 22.3 |
| SURELEASE[c] | 3.0 |
| TiO$_2$ | 5.6 |
| HPMC | 0.6 |
| Total | 158.1 |
| IR Granule Formulation | |
| Donepezil HCl | 10 |
| MCC CEOLUS ® KG802[a] | 115 |
| PC-10 | 15 |
| Total | 140 |
| IR/SR Tablet-2 Formulation | |
| SR Portion | 158 |
| IR Portion | 140 |

TABLE 2-continued

Unit dose composition of IR/SR Tablet-2 (310 mg Tablet)

| Ingredients | Weight, mg |
|---|---|
| PVPP XL-10 | 10 |
| Magnesium Stearate | 2 |
| Total | 310 |

[a] CELPHERE ® CP305 (300-500 μm) and MCC CEOLUS ® KG802 were purchased from Asahi Kasei Chemicals Corporation, (Tokyo, Japan)
[b] EUDRAIGIT ® NE30D was purchased from Evonik Röhm GmbH (Darmstadt, Germany).
[c] SURELEASE ® (aqueous ethylcellulose dispersion) was purchased from Colorcon.
HPMC = hydroxypropyl methyl cellulose
PEG 400 = polyethylene glycol 400
MCC = microcrystalline cellulose
PVPP XL-10 = polyvinyl polypyrrolidone, Copovidone 1.5 In Vitro Dissolution Performances of the IR/SR Tablets of Examples 1.3 and 1.4

The in vitro dissolution profiles of the SR pellets of Example 1.2 and IR/SR tablets of Examples 1.3 and 1.4 were obtained under simulated gastric condition. The dissolution tests were performed in 0.1N HCl (pH 1.2) solution at a temperature of 37° C. Samples of dissolution media were collected at predetermined intervals and analyzed by high performance liquid chromatography (HPLC) to obtain the dissolution profile. The dissolution profile of memantine contained in both SR portions 1 and 2 are summarized in Table 3, whereas the dissolution profiles of memantine and donepezil contained in both IR/SR Tablet-1 and IR/SR Tablet-2 are provided in Tables 4 and 5, respectively.

TABLE 3

In Vitro Dissolution Profile of Memantine from SR portions of Example 1.1 in 0.1N HCl

| | SR portion-1 | | SR portion-2 | |
|---|---|---|---|---|
| T (hr) | Mean Diss, % | SD | Mean Diss, % | SD |
| 0 | 0 | 0 | 0 | 0 |
| 1 | 7.7 | 1.00 | 9.1 | 1.05 |
| 2 | 13.5 | 2.04 | 12.5 | 1.00 |
| 3 | 25.0 | 1.60 | 17.1 | 0.15 |
| 4 | 37.6 | 2.84 | 30.7 | 5.07 |
| 6 | 67.6 | 3.18 | 36.3 | 1.97 |
| 8 | 92.3 | 6.88 | 53.6 | 4.10 |
| 12 | 102.4 | 4.04 | 74.5 | 0.90 |

TABLE 4

In Vitro Dissolution Profile of Memantine from IR/SR Tablets of Examples 1.3 and 1.4 in 0.1N HCl

| | Tablet-1, 5 kg | | Tablet-1, 6 kg | | Tablet-1, 8 kg | | Tablet-2 | |
|---|---|---|---|---|---|---|---|---|
| T (hr) | Mean Diss, % | SD | Mean Diss, % | SD | Mean Diss, % | SD | Mean Diss, % | SD |
| 0 | 0 | 0 | 0 | 0 | 0 | 0 | 0 | 0 |
| 1 | 18.2 | 3.75 | 20.2 | 1.48 | 39.4 | 2.58 | 13.9 | 0.81 |
| 2 | 44.8 | 6.41 | 46.0 | 2.25 | 71.7 | 5.01 | 21.4 | 1.38 |
| 3 | 65.2 | 7.79 | 69.3 | 1.15 | 85.4 | 9.13 | 34.1 | 2.73 |
| 4 | 76.1 | 8.26 | 78.7 | 3.83 | 95.5 | 3.22 | 45.3 | 4.83 |
| 6 | 105.1 | 6.88 | 94.8 | 3.76 | 108.5 | 3.03 | 54.7 | 0.17 |
| 8 | 101.9 | 1.81 | 94.7 | 2.83 | 116.5 | 11.14 | 69.0 | 3.38 |
| 12 | 109.2 | 1.00 | 104.1 | 3.21 | 113.1 | 11.97 | 93.2 | 5.23 |

TABLE 5

In Vitro Dissolution Profile of Donepezil from IR/SR Tablets of Examples 1.3 and 1.4 in 0.1N HCl

| T | Tablet-1, 5 kg | | Tablet-1, 6 kg | | Tablet-1, 8 kg | | Tablet-2 | |
|---|---|---|---|---|---|---|---|---|
| (min) | Mean Diss, % | SD | Mean Diss, % | SD | Mean Diss, % | SD | Mean Diss, % | SD |
| 0 | 0 | 0 | 0 | 0 | 0 | 0 | 0 | 0 |
| 15 | 96.1 | 6.2 | 100.5 | 1.4 | 99.2 | 3.4 | 101.4 | 2.6 |
| 30 | 97.1 | 6.5 | 102.5 | 1.2 | 104.0 | 5.4 | 101.0 | 0.3 |
| 60 | 98.6 | 7.2 | 104.4 | 2.1 | 105.2 | 1.3 | 101.2 | 1.0 |

The results summarized in Table 3 indicated that for the SR portions alone, at least about 80% of memantine remained un-released (i.e., remained in the SR coating) after contacting simulated gastric condition for 2 hours, and over 60% of memantine were released after 12 hours for both SR portions 1 and 2.

Regarding IR/SR tablets-1 having a hardness of 5 and 6 kg, the data in Table 4 demonstrated about 40% of memantine was released after contacting simulated gastric condition for 2 hours, and over 90% of memantine were released after 6 hours. In contrast, for IR/SR tablet having a hardness of 8 kg, about 70% of memantine was released after 2 hours. As to IR/SR tablet-2, more than about 70% of memantine remained in the SR coating after 2 hours, and over 90% of memantine were released after 12 hours. These results suggested that the compression pressure used for manufacturing the IR/SR tablet may affect the release behavior of memantine. As such, it is preferable in some embodiments that the compression pressure remained lower than 8 kg.

As to IR portion, all tablets listed in Table 5 exhibited an immediate release pattern with over 80% of donepezil being released within an hour after contacting the simulated gastric condition. As to tablets produced by different compression pressures, the respective donepezil dissolution profiles were found to be similar.

In addition, each tablets of Examples 1.3 and 1.4 were split into two halves, and the dissolution profiles of each half of the tablets were assessed by HPLC analysis (data not shown). Results indicated that tablets after splitting into two equal halves still exhibited acceptable dissolution patterns that comply with the principles and spirits of the present disclosure.

Example 2

Pilot Pharmacokinetic (PK) Study with IR/SR Tablets of Example 1.3

Pilot PK study was carried out in Chinese subjects, each receiving a single-dose medication, either positive control formulation or the respective IR/SR formulations of Example 1.3 and 1.4; PK properties of memantine and donepezil in each test subjects were then measured and recorded, as well as incidences and severities of undesirable side effects associated therewith.

This open-label, single-center randomized trial was conducted by School of Pharmacy, Fudan University, Shanghai, People's Republic of China. Eighteen healthy, male adult Chinese subjects aged between 24 to 27 years old who met the inclusion and/or exclusion criteria as listed below were enrolled with informed consent.

Inclusion criteria:
Age: 18-40 years old, and the age differences among subjects in the same study group is less than 10;
Gender: male;
Weight: standard weight ±20%;
Physical condition: without prior histories of any heart, liver, kidney, gastrointestinal (GI) tract, neurologic, mental, or metabolism disorders; tested normal in physical examination, which includes electrocardiogram, blood pressure, heart rate, and respiratory pattern examination; and routine laboratory examination, which includes urine, blood, liver function, and kidney tests.
The enrolled subjects have not taken any drugs for at least two weeks prior to the administration of the first dose of study drug, which is either the IR/SR formulation of this disclosure or the control formulation; and are forbidden from ingestion of any tobacco- or nicotine-containing products, alcohol- and caffeine-containing beverages of foods and juices during the course of the study Exclusion Criteria:
History and/or physical findings of cardiac disorders, including bradycardia, conduction disturbance, sinus node syndrome, heart failure, hypertension, cardionosis, etc.
History and/or physical findings of sever or chronic liver diseases, sever or chronic kidney diseases, metabolic abnormalities (diabetes, hyperlipidemia), endocrine disorders, GI track disorders, hematological diseases, tumors, chronic inflammation, and autoimmune disorders
History of allergy or hypersensitivity
Habitual use of medications, including habitual use of Chinese herbal medicines
Blood donation within three months prior to the study The enrolled subjects were randomly allocated to three groups according to a computer-generated randomization schedule. Each subjects in Group 1 receive a positive control medicine (i.e., the immediate-release formulation of memantine and donepezil); whereas each subjects in Groups 2 and 3 respectively receive the IR/SR tablet-1 of Example 1.3 and IR/SR tablet-2 of Example 1.4. All subjects were required to fast for at least 10 hours prior to the administration of the medication so as to avoid any effects that might have been caused by food intake on the PK properties. Two subjects did not complete this study; specifically, subject No. 1 withdrew due to severe adverse responses to the administered medication, and subject No. 18 withdrew before the commencement of this study.

In Group 1, EBIXA® (containing 10 mg of memantine HCl, from Lundbeck) and ARICEPT® (containing 10 mg of donepezil HCl, from Eisai) were orally administered to each subject, followed by another dose of EBIXA® (10 mg) administered twelve hours after the initial administration. In contrast, IR/SR tablet-1 of Example 1.3 and IR/SR tablet-2 of Example 1.4 were orally administered to each subjects in Groups 2 and 3, respectively. Blood samples were drawn from each subject at pre-designated time points and plasma concentrations of memantine and donepezil were determined by HPLC-MS/MS.

PK properties including maximal plasma concentration ($C_{max}$), time to reach the peak concentration ($T_{max}$), time required for the plasma drug concentration to decrease by one half ($T_{1/2}$), apparent first order elimination or terminal rate constant (K or $K_{el}$), the area under the plasma concentration verses time curve from zero to the last measured time point ($AUC_{0-t}$), and the area under the plasma concentration verses time curve from zero to infinity ($AUC_{0-\infty}$) were assessed immediately before (0 hour) and at 0.5, 1, 2, 3, 4, 5, 6, 7, 8, 9, 10, 11, 12, 13, 14, 15, 16, 24, 36, 60, 84, 108, and 156 hours after drug administration. Blood samples were collected at two extra time points, i.e., 12.5 and 20 hrs, respectively for subjects in Group 1.

$C_{max}$ and $T_{max}$ were obtained directly by the visual inspection of each subjects' plasma concentration-time profile. The slope of the terminal log-linear portion of the concentration-time profile was determined by least-squares regression analysis and used as the elimination rate constant (K). $T_{1/2}$ was obtained from the formula, $t_{1/2}=\ln(2)/K$. The $AUC_{0-t}$ from time zero to the last measured time point (i.e., 156 hours after the initial administration) was calculated using the trapezoidal rule and the extrapolated AUC from the last measured time point to infinity ($AUC_{0-\infty}$) was to be determined as the ratio of the last measured concentration ($C_t$) to the elimination rate constant. The area under the plasma concentration-time from zero to infinity ($AUC_{0-\infty}$) was calculated as the sum of the $AUC_{0-t}$ plus the ratio of $C_t/K$.

The thus-obtained PK properties of memantine and donepezil are respectively summarized in Tables 6 and 7. Undesirable side effects experienced by the test subjects are listed in Table 8.

TABLE 6

PK Properties of Memantine

| No. | $T_{max}$ (h) | $C_{max}$ (ng/mL) | $T_{1/2}$ (h) | K (1/h) | $AUC_{0-t}$ (h * ng/mL) | $AUC_{0-\infty}$ (h * ng/mL) |
|---|---|---|---|---|---|---|
| Group 1* | | | | | | |
| 2 | 20 | 18.7 | 51.32 | 0.01214 | 1495.46 | 1793.67 |
| 3 | 24 | 23.4 | 45.97 | 0.01355 | 1715.53 | 1943.54 |
| 4 | 24 | 23.1 | 38.42 | 0.01621 | 1467.96 | 1614.74 |
| 5 | 16 | 24.0 | 39.19 | 0.01590 | 1631.81 | 1808.56 |
| 6 | 20 | 20.9 | 56.35 | 0.01106 | 1781.79 | 2223.19 |
| Mean | 20.8 | 22.02 | 46.25 | 0.01377 | 1618.51 | 1876.74 |
| SD | 3.35 | 2.19 | 7.73 | 0.00227 | 136.06 | 226.21 |
| Mean ± SD | 17.45-24.15 | 19.83-24.21 | 38.52-53.98 | — | 1482.45-1754.57 | 1650.53-2102.95 |
| Median | 20 | 23.1 | 45.97 | 0.01355 | 1631.81 | 1808.56 |
| Group 2 | | | | | | |
| 7 | 36 | 18.8 | 51.55 | 0.01209 | 1593.83 | 1919.85 |
| 8 | 24 | 13.9 | 55.55 | 0.01121 | 1350.84 | 1707.51 |
| 9 | 24 | 18.7 | 52.13 | 0.01195 | 1504.86 | 1793.53 |
| 10 | 24 | 17.4 | 87.13 | 0.00715 | 1642.07 | 2423.89 |
| 11 | 15 | 18.1 | 62.75 | 0.00993 | 1375.27 | 1705.65 |
| 12 | 14 | 14.5 | 39.71 | 0.01569 | 1254.68 | 1415.32 |
| Mean | 22.8 | 16.9 | 58.14 | 0.01134 | 1453.59 | 1827.63 |
| SD | 7.96 | 2.16 | 16.05 | 0.00281 | 151.05 | 336.01 |
| Mean ± SD | 14.84-30.76 | 14.74-19.06 | 42.09-74.19 | — | 1302.54-1604.64 | 1491.62-2163.64 |
| Median | 24 | 17.75 | 53.84 | 0.01158 | 1440.065 | 1750.52 |
| Group 3** | | | | | | |
| 13 | 16 | 7.4 | 50.08 | 0.01244 | 527.17 | 609.95 |
| 14 | 36 | 16.5 | 38.44 | 0.01621 | 1483.85 | 1673.25 |
| 15 | 24 | 18.3 | 43.02 | 0.01448 | 1502.19 | 1723.87 |
| 16 | 14 | 16.9 | 49.32 | 0.01263 | 1549.41 | 1843.88 |
| 17 | 24 | 12.9 | 71.59 | 0.00870 | 1454.69 | 2048.76 |
| Mean | 22.8 | 13.8 | 50.49 | 0.01289 | 1303.46 | 1579.94 |
| SD | 8.67 | 4.39 | 12.73 | 0.00280 | 435.32 | 561.19 |
| Mean ± SD | 14.13-31.47 | 9.41-18.19 | 37.76-63.22 | — | 868.14-1738.78 | 1018.75-2141.13 |
| Median | 24 | 16.5 | 49.32 | 0.01263 | 1483.85 | 1723.87 |

*Subject no. 1 did not take the second dose of EBIXA ® (10 mg) due to severe side effects; hence, the data of subject no. 1 regarding PK properties of memantine is excluded.
**Subject no. 18 withdrew from the study before taking any drug.

TABLE 7

PK Properties of Donepezil

| No. | $T_{max}$ (h) | $C_{max}$ (ng/mL) | $T_{1/2}$ (h) | K (1/h) | $AUC_{0-t}$ (h * ng/mL) | $AUC_{0-\infty}$ (h * ng/mL) |
|---|---|---|---|---|---|---|
| Group 1 | | | | | | |
| 1 | 2 | 15.3 | 39.87 | 0.01562 | 602.73 | 652.52 |
| 2 | 3 | 18.4 | 57.02 | 0.01093 | 608.07 | 722.47 |
| 3 | 2 | 20.6 | 63.07 | 0.00988 | 847.49 | 1049.95 |
| 4 | 3 | 26.7 | 45.36 | 0.01374 | 824.62 | 916.36 |
| 5 | 1 | 29.2 | 75.74 | 0.00823 | 1040.34 | 1363.71 |
| 6 | 4 | 17.3 | 64.93 | 0.00960 | 874.25 | 1111.86 |
| Mean | 2.5 | 21.25 | 57.66 | 0.01133 | 799.58 | 969.48 |
| SD | 1.0 | 5.52 | 13.24 | 0.00280 | 168.46 | 263.24 |
| Mean ± SD | 1.5-3.5 | 15.73-26.77 | 44.42-70.9 | — | 631.12-968.04 | 706.24-1232.72 |
| Median | 2.5 | 19.5 | 60.045 | 0.010405 | 836.055 | 983.155 |
| Group 2 | | | | | | |
| 7 | 1 | 24.5 | 57.67 | 0.01080 | 848.06 | 1023.01 |
| 8 | 2 | 25.7 | 46.15 | 0.01350 | 989.57 | 1112.54 |
| 9 | 3 | 25.6 | 73.29 | 0.00850 | 814.62 | 1056.97 |

TABLE 7-continued

PK Properties of Donepezil

| No. | $T_{max}$ (h) | $C_{max}$ (ng/mL) | $T_{1/2}$ (h) | K (1/h) | $AUC_{0-t}$ (h * ng/mL) | $AUC_{0-\infty}$ (h * ng/mL) |
|---|---|---|---|---|---|---|
| 10 | 2 | 16.8 | 53.02 | 0.01175 | 821.87 | 958.02 |
| 11 | 1 | 30.2 | 54.09 | 0.01152 | 964.87 | 1095.10 |
| 12 | 2 | 23.4 | 43.46 | 0.01433 | 760.93 | 831.39 |
| Mean | 1.8 | 24.37 | 54.61 | 0.01173 | 866.65 | 1012.84 |
| SD | 0.75 | 4.37 | 10.55 | 0.00206 | 90.54 | 104.58 |
| Mean ± SD | 1.05-2.55 | 20-28.74 | 44.06-65.16 | — | 776.11-957.19 | 908.26-1117.42 |
| Median | 2 | 25.05 | 53.555 | 0.011635 | 834.965 | 1039.99 |
| | | | Group 3** | | | |
| 13 | 1 | 22.4 | 55.17 | 0.01129 | 828.21 | 964.59 |
| 14 | 2 | 18.5 | 50.74 | 0.01228 | 804.60 | 920.26 |
| 15 | 3 | 17.9 | 76.93 | 0.00810 | 944.92 | 1222.74 |
| 16 | 2 | 16 | 65.01 | 0.00958 | 830.94 | 1025.04 |
| 17 | 1 | 17 | 57.67 | 0.01080 | 778.75 | 958.31 |
| Mean | 1.8 | 18.36 | 61.11 | 0.01041 | 837.48 | 1018.20 |
| SD | 0.84 | 2.45 | 10.25 | 0.00162 | 63.64 | 120.35 |
| Mean ± SD | 0.96-2.64 | 15.91-20.81 | 50.86-71.36 | — | 773.84-901.12 | 897.85-1138.55 |
| Median | 2 | 17.9 | 57.67 | 0.01080 | 828.21 | 964.59 |

**Subject no. 18 withdrew from the study before taking any drug.

TABLE 8

Side Effects Experienced by Test Subjects

Group 1

1 Significant gastrointestinal discomfort; nausea; vomiting; headache.
2 Obvious gastrointestinal discomfort; nausea; dizziness; asthenia.
3 Nausea; vomiting (3 times); dizziness.
4 Chills; sweats; dizziness; headache; gastrointestinal discomfort; nausea; anorexia.
5 Chills; insensible sweats; nausea; dizziness; asthenia; vomiting (twice); anorexia.
6 Gastrointestinal discomfort; nausea; dizziness.

Group 2

7 Nausea; dizziness.
8 Nausea; chills; insensible sweats.
9 Mild gastrointestinal discomfort; nausea; dizziness; somnolence.
10 Dizziness; asthenia; fatigue; chills; nausea.
11 Dizziness; nausea.
12 No obvious side effects.

Group 3

13 Dizziness; insensible sweats; gastrointestinal discomfort; nausea; anorexia.
14 No obvious side effects.
15 Dizziness; nausea.
16 No obvious side effects.
17 Dizziness; nausea; chills.

Results summarized in Table 6 revealed that some PK properties of memantine derived from subjects administered with IR/SR tablets of this disclosure were significantly different from those derived from positive control subjects, i.e., subjects administered with commercially available memantine-containing formulation.

For example, the mean maximal plasma concentrations ($C_{max}$) of memantine derived from subjects administered with IR/SR tablet-1 (i.e., Group 2 subjects; mean $C_{max}$=16.9) or IR/SR tablet-2 (i.e., Group 3 subjects; mean $C_{max}$=13.8) are lower than that of the control subjects, or subjects administered with EBIXA® (i.e., Group 1 subjects; mean $C_{max}$=22.02). Also, the median $C_{max}$ of memantine derived from Group 2 subjects (median $C_{max}$=17.75 ng/mL) or Group 3 subjects (median $C_{max}$=16.5 ng/mL) are lower than that of Group 1 subjects (median $C_{max}$=23.1 ng/mL). Judging from the mean $C_{max}$, median $C_{max}$ and mean±standard deviation of $C_{max}$, the $C_{max}$ of memantine derived from Group 1 subjects is statistically different from that derived from both Groups 2 and 3 subjects.

Further, the time required reaching the peak concentration ($T_{max}$) of memantine in subjects administered with IR/SR tablet-1 (mean $T_{max}$=22.8; median $T_{max}$=24) or IR/SR tablet-2 (mean $T_{max}$=22.8; median $T_{max}$=24) is longer than that of the control subjects (Group 1; mean $T_{max}$=20.8; median $T_{max}$=20). As such, the $T_{max}$ of memantine derived from Group 1 is statistically different from that derived from both Groups 2 and 3. It is inferred that the reduced maximal plasma concentration in connection with the extended time to reach the peak concentration may be advantageous in ameliorating the undesired side effects.

In contrast, data summarized in Table 6 revealed that the $AUC_{0-t}$ and the $AUC_{0-\infty}$ of memantine derived from subjects taking either IR/SR tablet-1 or IR/SR tablet-2 are quite similar to those derived from control subjects, i.e., subjects administered with EBIXA®, which suggest that the IR/SR tablet-1 and IR/SR tablet-2 of this disclosure respectively possess similar therapeutic effect as that of EBIXA®.

Statistically, the PK properties of donepezil, as summarized in Table 7, do not differ significantly among the three groups. Assuming that the data distribution is approximately normal, then about 68% of the data values are within one standard deviation of the mean (mathematically, μ±σ, where μ is the arithmetic mean and σ is one standard deviation). In the present case, the "μ±σ" of $C_{max}$ of donepezil derived from Groups 1, 2 and 3 subjects are respectively 21.25±5.52 (15.73-26.77), 24.37±4.37 (20-28.74) and 18.36±2.45 (15.91-20.81), and these ranges substantially overlap with one another indicating that at least the PK properties for the immediate-release portion of the IR/SR formulation of this invention is comparable to the control medicine, which is also a fast-release formulation. In addition to the $C_{max}$, the $AUC_{0-t}$ and $AUC_{0-\infty}$ of donepezil in these three groups are also comparable to one another.

As can be seen in Table 8, incidences of side effects experienced by Group 1 subjects are significantly higher than those of Groups 2 and 3 subjects. Further, the extent of the side effects was less severe for subjects in Groups 2 and 3.

In view of the foregoing, the formulation as well as the method of the present disclosure may achieve the desired therapeutic effect while ameliorating the side effects experienced by the patient.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating a patient suffering from dementia or Alzheimer's disease comprising:
administering to the patient an oral dosage formulation as defined in Table 1 or 2, wherein the formulation provides an average blood level $C_{max}$ of memantine in a range of about 10-24 ng/mL during an average $T_{max}$ of about 10-45 hours, and an average blood level $C_{max}$ of donepezil in a range of about 12-38 ng/mL during an average $T_{max}$ of less than about 4 hours;

TABLE 1

| Ingredients | Weight, mg |
|---|---|
| Sustained Release (SR) Pellet-1 Formulation | |
| microcrystalline cellulose | 100 |
| Memantine HCl | 20 |
| hydroxypropyl methyl cellulose | 6.0 |
| Polyethylene glycol | 0.6 |
| Subtotal | 126.6 |
| SR-Coating-1 Formulation | |
| microcrystalline cellulose | 31.7 |
| Talc | 31.7 |
| hydroxypropyl methyl cellulose | 0.8 |
| Total | 190.7 |
| Immediate Release (IR) Granule-1 Formulation | |
| Donepezil HCl | 10 |
| microcrystalline cellulose | 115 |
| Pre-gelatinized starch | 15 |
| Total | 140 |
| IR/SR Tablet-1 Formulation | |
| SR Pellet-1/SR-Coating-1 | 190 |
| IR Granule-1 | 140 |
| polyvinyl polypyrrolidone | 10 |
| Magnesium Stearate | 2 |
| Total | 342 |

TABLE 2

| Ingredients | Weight, mg |
|---|---|
| SR Pellet-2 Formulation | |
| Polymethyl methacrylate | 100 |
| Memantine HCl | 20 |
| hydroxypropyl methyl cellulose | 6.0 |
| Polyethylene glycol | 0.6 |
| Subtotal | 126.6 |
| SR-Coating-2 Formulation | |
| microcrystalline cellulose | 22.3 |
| Ethyl cellulose | 3.0 |
| $TiO_2$ | 5.6 |
| hydroxypropyl methyl cellulose | 0.6 |
| Total | 158.1 |
| IR Granule-2 Formulation | |
| Donepezil HCl | 10 |
| microcrystalline cellulose | 115 |
| Pre-gelatinized starch | 15 |
| Total | 140 |
| IR/SR Tablet-2 Formulation | |
| SR Pellet-2/SR-Coating-2 | 158 |
| IR Granule-2 | 140 |
| polyvinyl polypyrrolidone | 10 |
| Magnesium Stearate | 2 |
| Total | 310. |

2. The method of claim 1, wherein the average blood level $C_{max}$ of memantine is in a range of about 11-22 ng/mL during the average $T_{max}$ of about 12-42 hours, and the average blood level $C_{max}$ of donepezil is in a range of about 14-35 ng/mL during the average $T_{max}$ of less than about 3 hours.

3. The method of claim 1, wherein the average blood level $C_{max}$ of memantine is in a range of about 15-20 ng/mL during the average $T_{max}$ of about 20-24 hours, and the average blood level $C_{max}$ of donepezil is in a range of about 18-31 ng/mL during the average $T_{max}$ of less than about 2 hours.

4. The method of claim 1, wherein the formulation provides an $AUC_{0-t}$ of memantine in a range of about 1300-1800 ng·h/mL and an $AUC_{0-t}$ of donepezil in a range of about 700-1000 ng·h/mL, wherein t is 156 hours after the administration of the oral dosage formulation.

5. The method of claim 1, wherein the oral dosage formulation is administered once a day or once every two days.

6. The method of claim 1, wherein the dosage formulation is in a form of a tablet or a caplet.

7. The method of claim 6, wherein the tablet is a scoring tablet having a score line at the center of the tablet for breaking the tablet into two equal parts.

8. The method of claim 1, wherein the formulation produces fewer incidents of one or more side effects selected from the group consisting of dizziness, headache, fatigue, asthenia, somnolence, chills, insensible sweats, anorexia, gastrointestinal discomfort, nausea, and vomiting; as compared with the side effects induced by the control formulation, in which both the memantine and donepezil are respectively provided in a form of an immediate-release formulation.

* * * * *